US00PP08636P

United States Patent [19]

Cobia

[11] Patent Number: Plant 8,636

[45] Date of Patent: Mar. 8, 1994

[54] CACTACEAE PLANT 'HEATHER'

[76] Inventor: Barnell L. Cobia, P.O. Box 771369, Winter Garden, Fla. 34777-1369

[21] Appl. No.: 35,328

[22] Filed: Mar. 22, 1993

[51] Int. Cl.[5] ..... A01H 5/00

[52] U.S. Cl. ..... Plt./88.5

[58] Field of Search ..... Plt. 88.5

*Primary Examiner*—James R. Feyrer

*Attorney, Agent, or Firm*—Roger L. Martin

[57] ABSTRACT

A new and distinct plant variety of the Cactaceae family is of the type known commercially as a "Spring Cactus" or "Easter Cactus" and has a growth habit which is similar to that of the 'Scarlet O'Hara' variety but which, nevertheless, differs, among other things, by having phylloclades with shorter midribs, and sterile flowers with fewer tube laminating tepals, tube forming tepals that are shorter and wider, tepals dominated by hues of purplish pink and purplish red, and an ovary with shorter length dimensions.

2 Drawing Sheets

BACKGROUND OF THE INVENTION

The invention relates to a new and distinct plant variety of the Cactaceae family which has been named *Rhipsalidopsis gaertneri* 'Heather' by the inventor.

Certain plant varieties of the Cactaceae family are well known in the foliage plant market and among these are those which are commonly referred to as the Spring or Easter cactus varieties because they tend to bloom in the Spring of the year.

The Spring cactus varieties on the market have blooms which vary in color from one variety to the next and are generally dominated by a red or closely related hue. One such cultivar in the marketplace at the time of application is 'Scarlet O'Hara' having a red flower.

SUMMARY OF THE INVENTION

A general objective has been to develop a new plant variety which is distinguishable from the 'Scarlet O'-Hara' variety and which is capable of being marketed competitively therewith.

The objective has been fully realized in the development of the new plant variety hereinafter described in detail. The new plant variety was developed in a nursery located at Winter Garden, Fla., as an offspring secured by cross-pollinating the flower of the variety known in the market as 'China Pink' with the pollen from the flower of the variety known in the market as 'Scarlet O'Hara'. The seeds taken from the fertilized seed pod ('China Pink'×'Scarlet O'Hara') were cultivated at the mentioned nursery location and after prolonged observation of the seedlings, the hybridized plant of the new variety was selected and asexually reproduced by propagation of cuttings taken from the original hybrid.

The paternal variety is similar in growth habit to the new plant variety, but in general has larger phyllocalades and blooms that are dominated by color hues that are generally red. The maternal variety is less upright than the new variety, and in general, has smaller phylloclades and blooms. Both parents of the new variety are fertile whereas the new plant variety is sterile.

Through successive propagation of cuttings taken from the seedling of the new variety, it has been ascertained that specimens of the new plant variety generally resemble the 'Scarlet O'Hara' variety in most respects but are distinguishable from this variety and from other related varieties known to the inventors by a growth habit which is evident in plant specimens on the new plant variety that have been propagated and grown under nursery conditions utilized in the growing of tropical plants in Winter Garden, Fla., as combining the following principal characteristics:

1. An erect growth habit,
2. Phylloclades which, in comparison to the 'Scarlet O'Hara' variety, have midribs with generally shorter length dimensions,
3. Flowers which, in comparison to the 'Scarlet O'Hara' variety, are sterile and have (a) generally fewer tube laminating tepals with generally shorter length dimensions, (b) a tube forming series of tepals with generally shorter length dimensions and having generally greater width dimensions, (c) tepals that are generally dominated by purplish pink and purplish red hues whereas the variety 'Scarlet O'Hara' is generally dominated by red hues, (d) an ovary with generally shorter length dimensions.

BRIEF DESCRIPTION OF THE DRAWINGS

The accompanying drawings serve by color photographic means to illustrate the new plant variety and wherein one sheet shows a 10 month old specimen which was grown from the propagation of a single phylloclade in a conventional 3½" plastic pot (trade designation) found in the marketplace. A second sheet shows an enlargement of a fully open bloom taken from the specimen shown in the first sheet in comparison with a second bloom also taken from the specimen shown in the first sheet and sectioned generally longitudinally through the perianth tube and ovary to expose the style and stamen arrangement.

DETAILED PLANT DESCRIPTION

The following is a detailed description of the new plant variety with colors and hues, unless otherwise clearly indicated by the text as, for example, through the absence of color notations, being named in accord with the ISCC-NBS Method of Designating colors (U.S. Dept. of Commerce, National Bureau of Standards, Circular 553), the named colors being interpreted from color specimens of the Munsell Book of Color. The description is further based on observations of well fertilized plants of about 10 months of age from initial propagation which were grown under 50%-75% shaded greenhouse nursery conditions in the Winter Garden, Fla. area and wherein temperatures range from 60°-85° F. during the winter months, from 75°-95° F. during the summer months, and are ambient during the intervening periods.

I. Name: *Rhipsalidopsis gaertneri* 'Heather'.

II. Parentage: The new variety is the result of a cross pollination between *Rhipsalidopsis rosea* 'China Pink' (maternal) and *Rhipsalidopsis gaertneri* 'Scarlet O'-Hara' (paternal). The resulting seeds were germinated under greenhouse conditions in Winter Garden, Fla. with one seedling being isolated as the new variety.

III. Classification:

A. *Botanic* (*Tropica, Roehrs Company, New Jersey* 1978).—(1) Family: Cactacea. (2) Tribe: Cereeae. (3) Sub-Tribe: Rhipsalidanae. (4) Genus: Rhipsalidopsis. (5) Species: *gaertneri.*

B. *Commercial.*—Spring or Easter cactus.

IV. Form: Epiphytic and terrestrial, shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and lateral wings having crenate margins.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — extends longitudinally of phylloclade and continuously through joints and with a laterally tapering cortex at the wing insertions. Pith surrounding vascular bundles that branch and provide lateral extensions of the vascular system to the marginal rounded teeth. (b) Texture — Smooth, waxy epidermis with wax in small embedded scales and becoming woody in basal stem areas with specimen aging. (c) Size (at maturity) — 1. Length: Range: 30–60 mm. Mean: 44.2 mm. Std. Dev.: 6.92 mm. 2. Thickness: Range: 2–5 mm. Mean: 3.6 mm. Std. Dev.: 0.88 mm. (d) Color (at maturity) — Usually dominated by yellow green and/or olive green hue. Commonly strong yellow green (7.5 GY 7/8(7.5 GY 6/8), moderate yellow green (7.5 GY 5/6), and/or moderate olive green (7.5 GY 4/6). (3) Wings: (a) Crenate and generally flattened from midrib cortex to tooth insertions and with slight thinning taper towards margins. (b) Margins — Crenate. (c) Texture — Succulent to leathery with smooth, waxy epidermis where the wax is arranged in small embedded scales of higher density than in midrib area, and becoming corky in the basal stem area, and becoming corky in the basal stem areas with specimen aging. (d) Size (at maturity) — 1. Width: Range: 8–15 mm. Mean: 10.8 mm. Std. Dev.: 1.86 mm. 2. Thickness: Range: 1.5–4.0 mm. Mean: 2.6 mm. Std. Dev.: 0.75 mm. (e) Color (at maturity) — Usually dominated by a yellow green and/or olive green hue. Commonly moderate yellow green (7.5 GY 5/6) and/or moderate olive green (7.5 GY 4/6) (7.5 GY 4/4). (4) Teeth: (a) Shape — 1. General: Generally flattened and tapered along the margins and from the wing insertions to the margin, and are crenate in shape. (b) Orientation — Generally project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Range: 1–2 mm. Mean: 1.2 mm. Std. Dev.: 0.31 mm. (f) Number — Usually 6–9 per phylloclade. (g) Color (at maturity) — Usually dominated by an olive green hue. Commonly moderate olive green (7.5 GY 4/6) (7.5 GY 3/4). (5) Areoles: (a) Terminal areole — Large, elongated, oval shaped with several acicular bristles, and several buds that may mature into either new phylloclades or flowers. The opposite ends of the areoles are located adjacent to subsidiary areoles which are in turn located at the axils of the teeth at the distal end of the phylloclade. (b) Axillary areoles — Acicular bristles without glochidia but having copious, short, brownish, multicellular, wooly hairs, In aeroles located below the teeth at the distal end of the phylloclade, there is usually only one areole which is frequently latent.

VI. Buds: Unarmored, ovoid.

VII. Flowers:

A. *General.*—Sessile, zygomorphic, usually solitary, terminal, perfect and epigynous with double hypanthium and whorled tepals (undifferentiated sepals and petals) having a spiral emergence as a perianth that is nearly rotate in structure and having a short tube, provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly to lanceolate and providing greater length dimensions and broader apices. All members have a pointed tip and entire margins. (3) Texture: Succulent and glabrous outer whorl members and grading inwardly in whorl to silken blades with fleshy basal areas. (4) Number: Usually 5–7. (5) Size (at full bloom): (a) Length (base-tip dimensions) Range: Usually less than 21 mm. Mean: 8.5 mm. Std. Dev.: 5.79 mm. (b) Width (maximum) Range: Usually less than 7 mm. Mean: 4.5 mm. Std. Dev.: 1.16 mm. (6) Color (at full bloom): Members generally have a center field area that is usually dominated by a red hue which merges with a marginal blade area that is usually dominated by a pink and/or purplish pink hue. Commonly moderate red (2.5 R 4/8) and/or grayish red (2.5 R 4/6) in tepal center field area, and becoming moderate purplish ed (10 RP 5/10) and/or deep pink (10 RP 6/10) in the marginal blade areas. (7) Orientation: Generally erect at full bloom.

C. *Tube laminating series.*—(1) General: Tepals inserted on ovary and basally united below the throat as outer lamination on the perianth tube and with progressively greater amount of basal fusion inwardly in the whorl. (2) Shape: Zygomorphic and grading inwardly in the whorl with progressively greater length dimensions with a blade area that is generally lanceolate and having acute to acuminate tips and entire margins. (3) Texture: Glabrous, silken blades with slightly fleshy basal areas. (4) Number: Usually 5–7. (5) Size (at full bloom) — (a) Length (base-tip dimension) Range: 7–42 mm. Mean: 29.7 mm. Std. Dev.: 8.56 mm. (b) Width (maximum) — Range: 5–8 mm. Mean: 6.7 mm. Std. Dev.: 0.84 mm. (6) Color (at full bloom): (a) General — Tepals with a basal area that is usually dominated by a yellowish green and/or purplish pink hue immediately above insertion that merges distally into a center blade area that is usually dominated by a purplish pink and/or purplish red hue. Center blade area then continues to merge distally into a marginal blade area that in color is usually dominated by a purplish pink and/or purplish red hue. (b) Basal area — Commonly pale yellowish green (10 Y 9/2) at insertion in outer whorl members and becoming moderate purplish pink (5 RP 7/8) in the inner whorl members. (c) Blade area — Commonly moderate purplish pink (5 RP 7/8), moderate purplish red (5 RP 5/10), and/or deep purplish pink (5 RP 6/10) in the center field areas and merging distally with the marginal blade area that is commonly deep purplish pink (7.5 RP 6/10) and/or moderate purplish red (7.5 RP 5/10). (7) Orientation: Generally ranging from being erect to being perpendicular to the perianth tube.

D. *Tube forming series.*—(1) General: Tepals basally united to form a short hollow perianth tube that is inserted on ovary. (2) Shape: (a) Perianth tube — Short and circular in cross section. (b) Blades — Nearly zygomorphic and generally lanceolate with acuminate to acute tips and entire margins. (3) Texture: (a) Perianth tube — Thick, succulent and slightly ribbed. (b) Blades — Translucent and silken. (4) Number: Usually 7–9. (5) Size (at full bloom): (a) Perianth tube — 1. Length (measured from top of ovary) Range: Usually 4–6 mm. Mean: 4.9 mm. Std. Dev.: 0.76 mm. 2. Diameter: Range: Usually 4.5–6 mm. Mean: 5.3 mm. Std. Dev.: 0.54 mm. (b) Blades — 1. Length (base-tip): Range: 31–42 mm. Mean: 35.7 mm. Std. Dev.: 3.16 mm. 2. Width (maximum): Range: 6–10 mm. Mean: 7.6 mm. Std. Dev.: 1.09 mm. (6) Color (at full bloom): (a) Perianth tube — A basic field that is generally dominated by a yellowish green and/or yellowish white hue. Commonly pale yellowish green (10 Y 9/2) (10 Y 9/1) and/or yellowish white (10 Y 9/1). (b) Blades — A center blade area that is generally dominated by a purplish pink and/or purplish red hue, and merging distally with a marginal blade area that is generally dominated by a purplish pink and/or purplish red hue. Generally dominated by a purplish pink hue in the basal area at insertion. Commonly deep purplish pink (5 RP 6/10) and/or moderate purplish red (5 RP 5/10) in the center field areas and becoming deep purplish pink (7.5 RP 6/10) and/or moderate purplish red (7.5 RP 5/10) in the marginal blade areas. Commonly moderate purplish pink (5 RP 7/8) and/or light purplish pink (5 RP 8/6) at insertion. (7) Orientation: Obtuse to recurve.

E. *Androecium (stamen).*—(1) General: Numerous exerted and diadelphous stamens having filaments basally fused to the perianth tube, thin annuluar around the style and which is provided with thin, deflexed, irregular, toothed margin or ruffle at the throat of the annulus. (2) Stamen number: Usually 116–153. (3) Filaments: (a) General — Translucent with anther connective. (b) Shape — Long, slender, terete. (c) Texture — Glabrous and capillaceous. (d) Color — Generally dominated by a reddish purple hue at the distal end and merging with a purplish pink hue intermediate the opposing ends and becoming a yellowish white and/or yellowish green hue in the basal area. Commonly strong reddish purple (2.5 RP 5.10) (2.5 RP 4/10) in the disal end, becoming moderate purplish pink (5 RP 7/8) and/or deep purplish pink (5 RP 6/10) in the intermediate area, and becoming pale yellowish green (10 y 9/2) (10 Y 9/1) and/or yellowish white (10 Y 9/1) in the basal area at insertion. (e) Size (at full bloom): 1. Length: Range: 8–21 mm. Means: 14.5 mm. Std. Dev.: 5.12 mm. 2. Diameter: Usually 0.10–0.25 intermediate opposite ends. (4) Anthers: (a) General — Adnate with four longitudinally dehiscent pollen sacs and connective inserted at end. (b) Shape — Elongated. (c) Texture — Waxy. (d) Color (before dehiscence) — Dominated by a greenish yellow hue. Commonly brilliant greenish yellow (10 Y 9/10) (10 Y 9/8) and/or greenish yellow (10 Y 9/8).

F. *Gynoecium (pistil).*—(1) General: Exerted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a purplish pink hue at the distal end and intermediate areas of the style, and merging into a purplish white hue in the basal area. Commonly deep purplish pink (5 RP 6/10) and/or moderate purplish pink (5 RP 7/8) at the distal end and intermediate area and becoming purplish white (5 RP 9/1) in the basal area at insertion. (e) Size (at full bloom) — 1. Length: Range: 13–16 mm. Mean: 14.3 mm. Std. Dev.: 1.04 mm. 2. Diameter: 0.50–0.75 mm. (3) Stigma: (a) General — exerted and erect to recurve with usually 5 marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Usually dominated by white and/or a purplish white hue. Commonly white (2.5 RP 9/0) (2.5 RP 9.5/0) and/or purplish white (5 RP 9/1). (e) Size — 1. Length: Range: 3–4.5 mm. Mean: 3.7 mm. Std. Dev.: 0.58 mm. (4) Ovary: (a) General — Inferior with thin epidermis and usually 5–6 carpules with numerous ovules. (b) Shape — Terete to ovoid and generally broadening from insertion to floral end. Generally having five (5) prominent longitudinal ribs, single concavity, and having an inserted style. (c) Texture — Succulent with glabrous thin outer epidermis. (d) Color — A basic field with color usually dominated by a yellow green hue with longitudinal ribs usually dominated by a red hue. Basic field is commonly strong yellow green (2.5 GY 6/8) and/or moderate yellow green (2.5 GY 6/6) (2.5 GY 5.6). Longitudinal ribs commonly moderate red (2.5 R 4/8) and/or grayish red (2.5 R 4/6). (e) Size — 1. Length: Range: 9–11 mm. Mean: 9.8 mm. Std. Dev.: 0.83 mm. 2. Major axis: Range: 9–11 mm. Mean: 9.9 mm. Std. Dev.: 0.64 mm. 3. Minor axis: Range: 7–9 mm. Mean: 8.2 mm. Std. Dev.: 0.63 mm.

VIII. Growth habit: Erect.

GENERAL DESCRIPTION OF A PLANT SPECIMEN

Age of plant: 10 months from initial propagation of single phylloclade, having been pruned to the 2 tier level at approximately 5 months of age.

Branches from propagated phylloclade: 7.

Total number of new phylloclades grown: 25.

GENERAL:

| Branch Number | No. of Phylloclades | Maximum Length | No. of Tips |
|---|---|---|---|
| 1 | 5 | 49 mm. | 4 |
| 2 | 1 | 51 mm. | 1 |
| 3 | 5 | 52 mm. | 4 |
| 4 | 3 | 37 mm. | 2 |
| 5 | 3 | 48 mm. | 2 |
| 6 | 5 | 58 mm. | 4 |
| 7 | 3 | 47 mm. | 2 |

MIDRIBS

| Branch Number | Average Midrib Length | Average Midrib Thickness |
|---|---|---|
| 1 | 41.6 mm. | 3.2 mm. |
| 2 | 46.0 mm. | 3.0 mm. |
| 3 | 50.6 mm. | 4.3 mm. |
| 4 | 43.3 mm. | 4.0 mm. |
| 5 | 50.0 mm. | 4.3 mm. |
| 6 | 43.2 mm. | 3.4 mm. |
| 7 | 36.0 mm. | 2.7 mm. |

WINGS

| Branch Number | Average Wing Thickness | Average Wing Width (maximum) |
|---|---|---|
| 1 | 2.4 mm. | 10.6 mm. |
| 2 | 1.5 mm. | 10.0 mm. |
| 3 | 3.1 mm. | 12.4 mm. |
| 4 | 2.8 mm. | 11.0 mm. |
| 5 | 3.3 mm. | 12.0 mm. |
| 6 | 2.4 mm. | 10.0 mm. |
| 7 | 1.7 mm. | 9.0 mm. |

Phylloclade color: Strong yellow green (7.5 GY 6/8), moderate yellow green (7.5 GY 5/6), and moderate olive green (7.5 GY 4/6) (7.5 GY 5/6) (7.5 GY 4/4) (7.5 GY 3/4).

GENERAL DESCRIPTION OF A FLOWER

The following is a general description of a flower of the new plant variety and which was in full bloom in April on a 10 month old plant specimen grown under shaded greenhouse conditions in Winter Garden, Fla.

Number of buds and blooms on plant specimen: 12.

Bloom life: 8 days.

Sepaloid series of tepals:

*Number.*—6.

*Tepal size (at full bloom).*—Maximum base-tip dimension: 19 mm. Minimum base-tip dimension: 5 mm. Maximum width dimension: 5.5 mm. Minimum width dimension: 3 mm.

*Color (at full bloom).*—Moderate red (2.5 R 4/8) and grayish red (2.5 R 4/6) in tepal center field area, and moderate purplish red (10 RP 5/10) and deep pink (10 RP 6/10) in the marginal blade areas.

Tube laminating series of tepals:

*Number.*—7.

*Size (at full bloom).*—Maximum base-tip dimension: 38 mm. Minimum base-tip dimension: 9 mm. Maximum blade width: 8 mm. Minimum blade width: 6.5 mm.

*Color (at full bloom).*—Pale yellowish green (10 Y 9/2) at insertion in outer whorl members and moderate purplish pink (5 RP 7/8) at insertion of inner whorl members. Moderate purplish pink (5 RP 7/8), moderate purplish red (5RP 5/10) and deep purplish pink (5 RP 6/10) in center field area. Deep purplish pink (7.5 RP 6/10) and moderate purplish red (7.5 RP 5/10) in marginal blade area.

Tube forming series of tepals:

*Number.*—9.

*Size (at full bloom).*—Perianth tube: Length: 6 mm. Diameter: 5 mm. Blades: Maximum length (base-tip): 40 mm. Minimum length (base-tip): 37 mm. Maximum blade width: 10 mm. Minimum blade width: 8 mm.

*Color (at full bloom).*—Perianth tube: Pale yellowish green (10 Y 9/1) and yellowish white (10 Y 9/1). Blades: Deep purplish pink (5 RP 6/10) and moderate purplish red (5 RP 5/10) in the center field areas, deep purplish pink (7.5 RP 6/10) and moderate purplish red (7.5 RP 5/10) in the marginal blade areas, and purlish pink (5 RP 7/8) at insertion.

Androecium:

*Stamen number.*—127.

*Filaments.*—Color: Strong reddish purple (2.5 RP 5/10) (2.5 RP 4/10) in the distal end, yellowish white (10 Y 9/1) at insertion, and moderate purplish pink (5 RP 7/8) and deep purplish pink (5 RP 6/10) in the intermediate areas.

*Size (at full bloom).*—Length: 16 mm. Diameter: about 0.20 mm. intermediate the opposite ends.

*Anthers.*—Color (before dehiscing): Brilliant greenish yellow (10 Y 9/10) (10 Y 9/8) and light greenish yellow (10 Y 9/8).

Gynoecium (pistil):

*Style.*—Color: Deep purplish pink (5 RP 6/10) and moderate purplish pink (5 RP 7/8) in the distal and intermediate areas, purplish white (5 RP 9/1) in the basal area at insertion. Size (at full bloom): Length — 15 mm. Diameter — About 0.50 mm. intermediate the opposite ends.

*Stigma.*—Color: White (2.5 RP 9.0) (2.5 RP 9.5/0). Size: 4 mm. (avg.) lobe length.

*Ovary.*—Color: Basic field is strong yellow green (2.5 GY 6/8) and moderate yellow green (2.5 GY 6/6) (2.5 GY 5/6). Longitudinal ribs moderate red (2.5 R 4/8) and grayish red (2.5 R 4/6). Size (at full bloom): Length (insertion to concavity base) — 11 mm. Major axis — 10 mm. at distal end of concavity. Minor axis — 9 mm. at distal end of concavity.

We claim:

1. A new and distinct plant variety of the Cactaceae family as shown and described and which is mainly distinguished from its antecedents and known related varieties by growth characteristics that are similar to those of the 'Scarlet O'Hara' variety but as modified by the combination of the following characteristics:

1. An erect growth habit,

2. Phyllocalades which, in comparison to the 'Scarlet O'Hara' variety, have midribs with generally shorter length dimensions, 3. Flowers which, in comparison to the 'Scarlet O'Hara' variety, are sterile and have (a) generally fewer tube laminating tepals with generally shorter length dimensions, (b) a tube forming series of tepals with generally shorter length dimensions, (c) tepals that are generally dominated by purplish pink and purplish red hues whereas the variety 'Scarlet O'Hara' is generally dominated by red hues, (d) an ovary with generally shorter length dimensions.

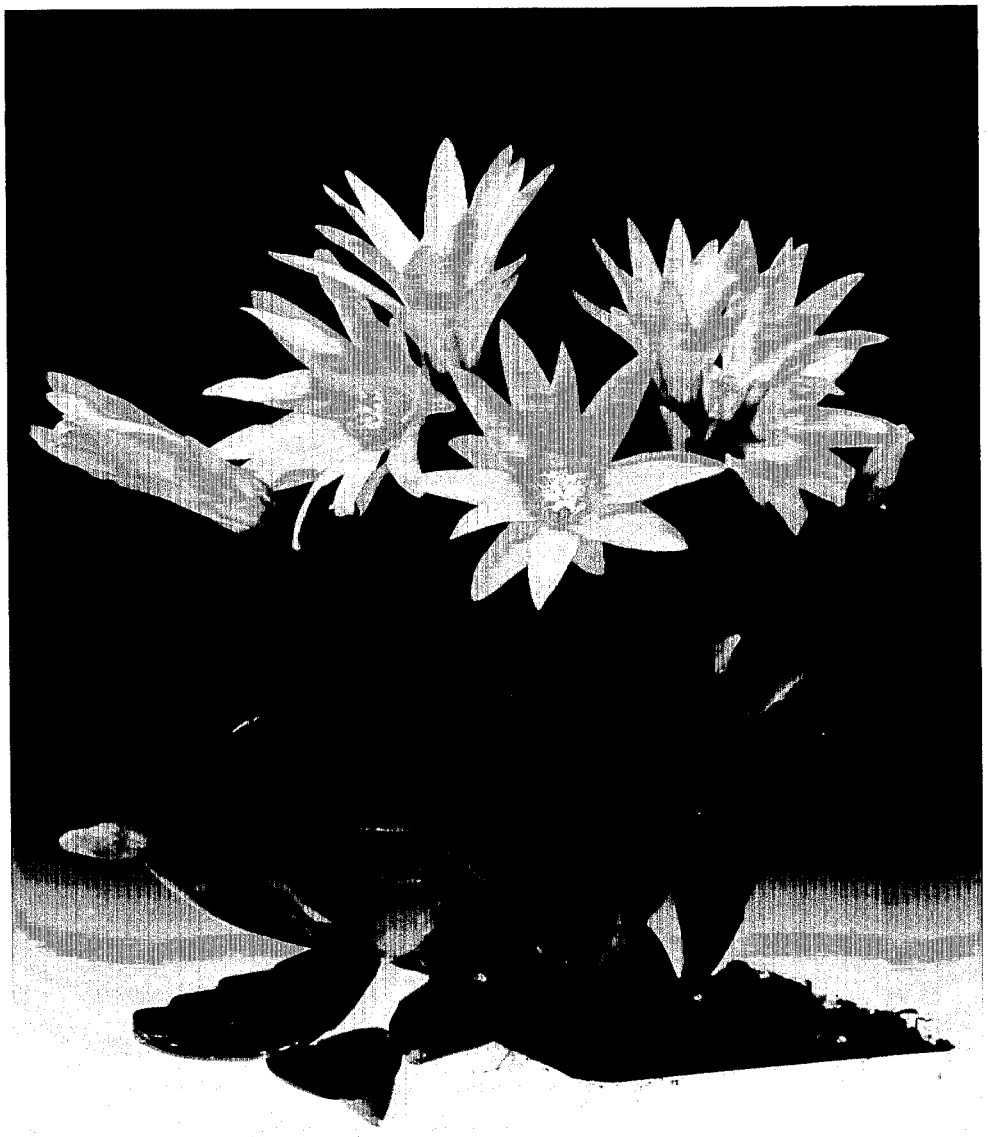

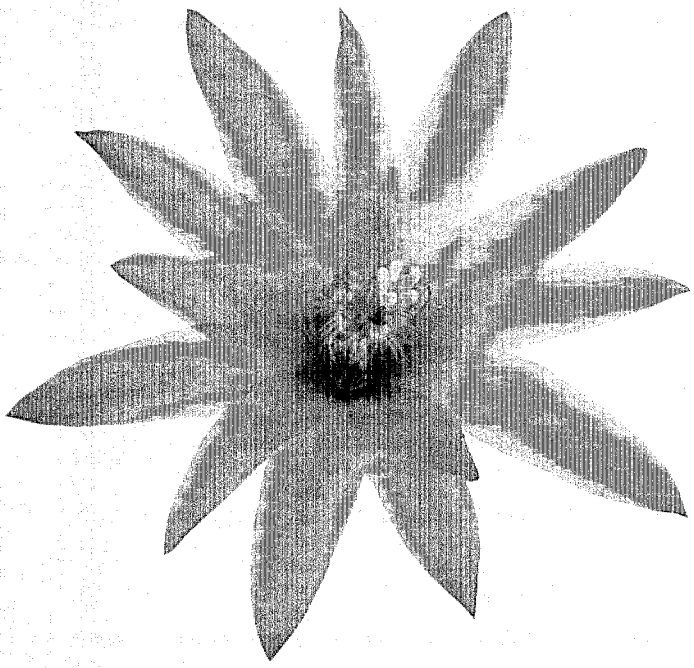
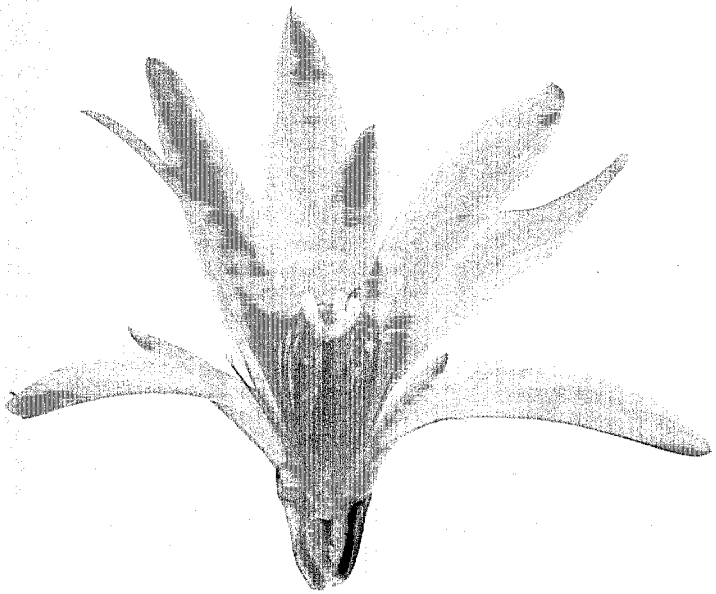

* * * * *